United States Patent [19]

Rooney et al.

[11] Patent Number: 4,741,868

[45] Date of Patent: May 3, 1988

[54] PRODUCTION OF SULFONATED ASPHALT

[75] Inventors: Patrick Rooney; Jeffrey A. Russell; Terry D. Brown, all of Bartlesville, Okla.

[73] Assignee: Phillips Petroleum Company, Bartlesville, Okla.

[21] Appl. No.: 708,142

[22] Filed: Mar. 4, 1985

[51] Int. Cl.$^4$ ............................................. C07C 143/24
[52] U.S. Cl. ............................. 260/505 R; 260/505 C; 208/44
[58] Field of Search .......... 208/44; 260/505 R, 505 C

[56] References Cited

U.S. PATENT DOCUMENTS 3,089,842  5/1983  Strahon ................................. 208/44

Primary Examiner—Alan Siegel
Attorney, Agent, or Firm—Paul S. Chirgott

[57] ABSTRACT

Sulfonated asphalt is produced by heating an asphaltic material, preferably having a softening point between about 315° F. and 350° F., by mixing the asphalt with a solvent, such as hexane, sulfonating the asphalt with a liquid sulfonating agent, such as liquid sulfur trioxide, neutralizing the sulfonic acids with a basic neutralizing agent, such as sodium hydroxide, separating solvent from the sulfonated asphalt, preferably by passing the same through a wiped film evaporator, recovering the evaporated solvent for reuse, preferably by passing the same in indirect heat exchange with a closed cycle refrigerant, recovering solvent from vapors from the sulfonation and neutralization steps by either scrubbing with neutralizing agent or sulfuric acid or by passing the same through fiber-type filter means and, thereafter, passing the same to the refrigeration step and drying the separated, sulfonated asphalt, preferably by passage through a drum dryer, and separating particle-form sulfonated asphalt from the vapors from the drum dryer, preferably by passing the same through a cyclone separator. Preferably the process is a batch-type process in which the rates of flow of the solvent, the asphaltic material, the sulfonating agent and the neutralizing agent and the periods of time prior to withdrawal of the sulfonic acids and the sulfonated asphalt are coordinated in accordance with a predetermined time cycle.

21 Claims, 2 Drawing Sheets

PRODUCTION OF SULFONATED ASPHALT

The present invention relates to the production of sulfonated asphalt. In another aspect, the present invention relates to the production of sulfonated asphalt particularly useful in the preparation of an oil well drilling fluid.

BACKGROUND OF THE INVENTION

Sulfonated asphalts are conventionally prepared by contacting the asphalt with a suitable sulfonating agent to produce sulfonic acids, neutralizing the sulfonic acids with a suitable neutralizing agent to produce sulfonated asphalt, separating the sulfonated asphalt from unreacted materials and any carrier materials or diluents, such as water from an aqueous acid or neutralizing agent, and drying the thus separated sulfonated asphalt. The dried sulfonated asphalt can then be utilized in the preparation of drilling fluids, such as aqueous, oil-base, and emulsion-types. Such drilling fluids have been found to have excellent rheological properties, such as viscosity and gel strength, and exhibit a low rate of filtration or fluid loss.

Since asphalt is generally semi-solid or solid in constituency, the very nature of this material creates numerous problems in a sulfonation process. One partial solution to this problem is to utilize asphalt which will have a relatively low softening point, thereby reducing the difficulties in handling and reacting the same. However, even with lower softening point asphalts, it is necessary to mix a diluent or solvent with the asphalt prior to sulfonation. Such solvents are generally selected so as to be inert (not sulfonatable themselves) and to have low boiling points so as to permit easy removal of the solvent from the sulfonated asphalt product. However, such selection of solvent in and of itself creates problems, to the extent that vapor phases containing significant amounts of solvent are produced in the sulfonation and neutralization steps and, where the solvent is recovered from these vapor streams, the recovery system itself produces a number of vapor phases containing lesser amounts of solvent all of which are conventionally vented to the atmosphere either continuously or intervally. Accordingly, these vapor phase streams not only result in substantial losses of solvent, but create serious pollution problems when vented to the atmosphere. Such solvents are often highly flammable and, therefore, also create safety hazards if not handled properly. Difficulties are also encountered in dispersing the asphalt in the solvent, as a result of which relatively large lumps of asphalt result in plugging of flow lines in the system, and reducing the degree of contact between the sulfonating and neutralizing agents and the asphalt and, thus, lowering conversion to sulfonated asphalt product. While, as previously indicated, lower softening point asphalts are advantageous from the standpoint of ease of handling and processing, higher softening point asphalts produce a sulfonated asphalt product having superior properties for use in drilling fluids. While the sulfonation and neutralization steps can be carried out continuously, the most effective operation utilizes batch-type sulfonation and neutralization steps. The inefficiencies of batch-type operations are well known but, in the production of sulfonated asphalts, these problems are somewhat exaggerated, to the extent that many of the steps involve manual operations and control. Numerous problems are also involved in the drying of the sulfonated asphalt product. Usually such drying is performed by a series of drum-type dryers. Since such dryers are often subject to air leakage and, to the extent that significant amounts of solvent are present, safety hazards as well as less effective recovery of solvent downstream of the dryers result. Such dryers also usually include steam stripping of the feed material and, accordingly, a vapor phase containing small amounts of particle-form sulfonated asphalt are carried by the vapor phase. This vapor phase is also normally vented to the atmosphere and, thus, creates additional air pollution problems. Finally, even with the most efficient systems for solvent recovery, a vapor phase is usually produced containing small amounts of solvent, which again is normally vented to the atmosphere, thus, again creating pollution problems as well as resulting in the loss of some of the solvent.

SUMMARY OF THE INVENTION

It is therefore an object of the present invention to provide a process for the production of sulfonated asphalt which overcomes the above-mentioned and other problems of the prior art. Another object of the present invention is to provide a process for the production of sulfonated, asphalt utilizing asphalt starting materials of higher softening point, to produce sulfonated asphalts adapted for use in drilling fluids of improved properties. Another and further object of the present invention is to provide a process for the production of sulfonated asphalt which results in improved recovery of solvents for reuse and effective and efficient use of non-recoverable solvents. A further object of the present invention is to provide a process for the production of sulfonated asphalt which essentially eliminates the venting of vapor streams containing solvents to the atmosphere. A still further object of the present invention is to provide a process for the production of sulfonated asphalt which reduces plugging of flow lines and equipment and, at the same time, improves conversion to sulfonated asphalt products. Another object of the present invention is to provide a process for the production of sulfonated asphalt which can effectively and efficiently be carried out as a batch-type operation. Yet another object of the present invention is to provide a process for the production of sulfonated asphalt wherein a batch-type operation is carried out automatically and efficiently. A further object of the present invention is to provide a process for the production of sulfonated asphalt which reduces the discharge of particulate sulfonated asphalt product to the atmosphere. Another object of the present invention is to provide a process for the production of sulfonated asphalt in which a saleable by-product can be produced during the recovery of solvent from the system. A still further object of the present invention is to provide a process for the production of sulfonated asphalt in accordance with any or all of the above-mentioned objects, while, at the same time, improving the safety of the operation. Yet another object of the present invention is to provide a process for the production of sulfonated asphalt which accomplishes any and all of the above-mentioned objectives, while, at the same time, reducing the discharge of pollutants to the atmosphere. These and other objects of the present invention will be apparent from the following description.

In accordance with the present invention, sulfonated asphalt is produced by adding a normally liquid, inert, low boiling solvent to an asphalt, preferably having a softening point between about 315° F. and 350° F., preferably producing a homogenized dispersion of the asphalt and the solvent, reacting the mixture of asphalt and solvent with a liquid form sulfonating agent, preferably liquid sulfur trioxide, neutralizing the sulfonic acids with a basic neutralizing agent, separating the solvent from the sulfonated asphalt, preferably by forming a moving film of the sulfonated asphalt on a heated surface under conditions adapted to simultaneously evaporate the solvent, recovering the separated solvent, preferably by indirect heat exchange with a closed cycle refrigerant, and drying the separated sulfonated asphalt as a product of the process.

DESCRIPTION OF THE PREFERRED EMBODIMENTS

Figure 1:
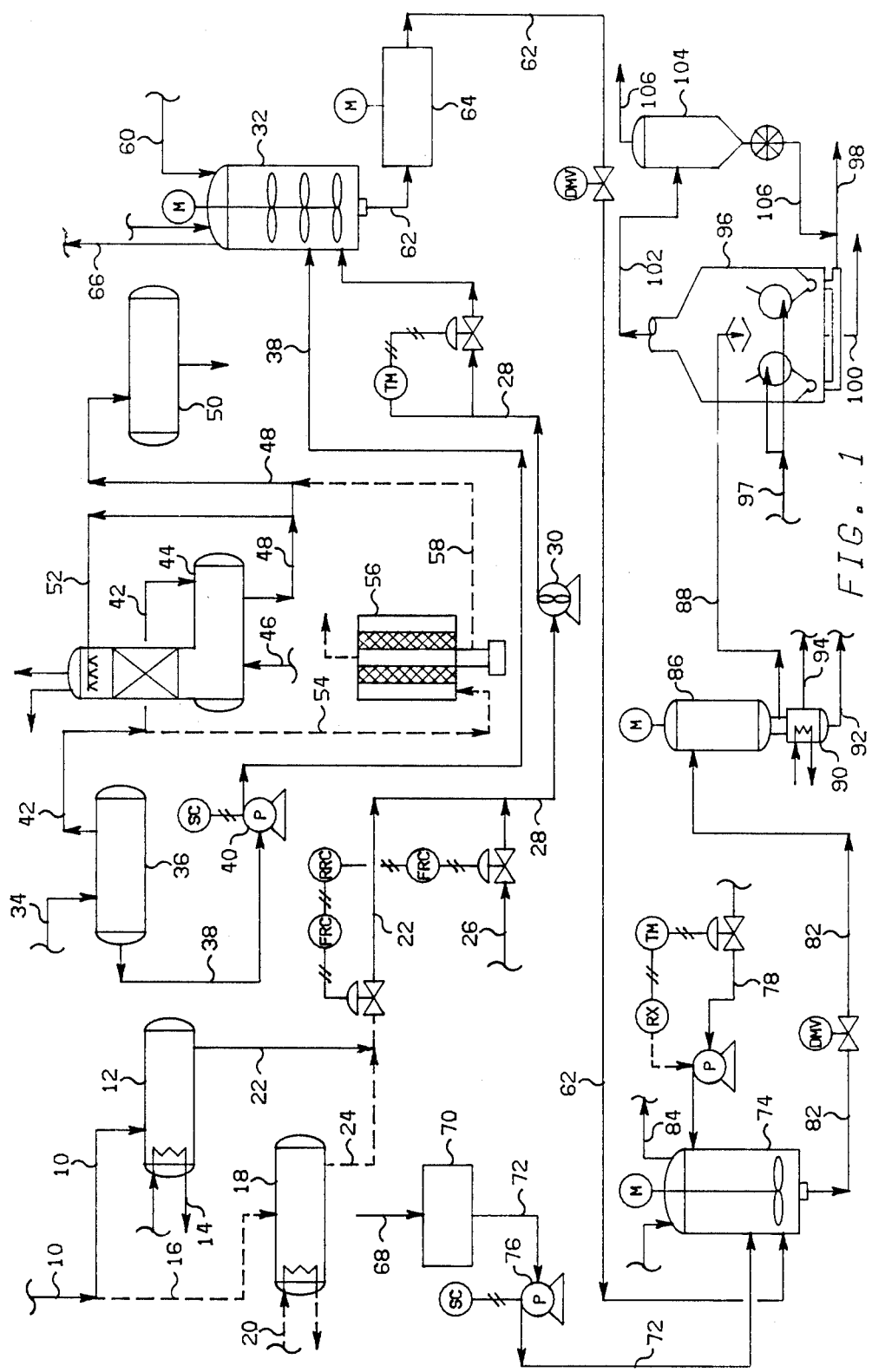
FIG. 1 of the drawings schematically shows a system for the production of sulfonated asphalt in accordance with the present invention.

The term "asphalt" or "asphaltic material", as used in the specification and the appended claims, is meant to cover dark brown to black semi-solid or solid cemetitious hydrocarbon materials which are completely or substantially soluble in carbon disulfide and in which bitumins are the sole or predominant constituent and these materials occurring in nature as such or being obtained by refining petroleum by distillation, precipitation, cracking, oxidation or similar operations. The terms "sulfonates", "sulfonated asphalt" and "sulfonated asphaltic material", as used in this specification, and the appended claims are meant to cover the ammonium, alkali metal, and alkaline earth metal salts of asphalt that have been sulfonated with a sulfonating agent.

Asphaltic materials useful in preparing the sulfonated asphalt of the present invention include asphaltenes, maltenes, blown asphalt, straight residual oils, distillation residues, still bottoms, cracking residues, asphaltic bitumins and the like. Preferred asphalts having ring and ball softening points in the range of about 115° F. to 475° F. can be utilized in accordance with the present invention. However, asphalts having softening points between about 315° F. and 350° F. are preferred.

In preparing the sulfonates, the asphaltic starting material in either semi-solid or solid constituency is preferably in a granulated, pulverized or finely divided form. The asphalt is generally heated, as by indirect heat exchange with steam or, preferably, for higher softening point, asphaltic materials, by indirect heat exchange with hot oil. A normally liquid, inert (non sulfonatible) diluent or solvent mixed with the heated asphalt. Preferably, the solvent is dried so as to permit the sulfonation to be carried out under anhydrous conditions. Suitable diluents or solvents include carbon tetrachloride, chloroform, pentane, n-hexane, octanes, gasoline, kerosene, cyclohexane, diesel fuel, sulfur dioxide and the like. However, a preferred solvent is a low boiling, normal, paraffinic hydrocarbon, preferably having a total of 5 to 8 carbon atoms per molecule and particularly hexane. The mixture of asphalt and solvent is, preferably, "delumped" to produce an essentially uniform dispersion of the asphalt in the solvent. An asphalt concentration of about 15% to 50% by weight and, preferably, 20-35 wt. percent is desirable.

Sulfonating agents which can be utilized in the sulfonation step include fuming sulfuric acid, chlorosulfonic acid, concentrated sulfuric acid and sulfur trioxide. However, a preferred sulfonated agent is liquid sulfur trioxide. Generally, liquid sulfur trioxide when used as a sulfonating agent will be employed in amounts between about 10 and 100 pounds for each 100 pounds of asphalt. In the sulfonation step, the asphaltic dispersion is passed to a suitable sulfonation zone, such as a stirred, externally cooled reactor, where it is sulfonated in the liquid-phase. The sulfonation reaction is practically instantaneous and exothermic. Accordingly, the temperature of the sulfonation reaction is controlled by the controlled addition of sulfonating agent and also by circulating a cooling medium in an external jacket surrounding the sulfonation reactor. The temperature will usually be controlled within the range of about 0° to 250° F., with the preferred operating range being between 32° and 100° F. Lower temperatures are somewhat preferred, since above about 200° F. excessive oxidation with liberation of sulfur dioxide may take place. The asphalt-sulfonating agent weight ratio will vary with the sulfonation temperature and the asphalt starting material but generally will be in the range of about 1/0.12 and 1/1. The sulfonation reacton is usually carried out at atmospheric pressure although pressures greater or less than atmospheric can be employed if desired.

The sulfonic acids produced in the sulfonation step are neutralized by contacting them with a suitable neutralizing agent, including an aqueous solution of a basic neutralizing agent selected from the group consisting of ammonia, alkali metal and alkaline earth metal salts, oxides and hydroxides. A preferred neutralizing agent is a 50% aqueous sodium hydroxide solution, which is added to the mixture containing sulfonic acids in a stirred reactor. The neutralization step can be conveniently carried out over a wide temperature range, for example, 200° F. to 240° F. and at a pressure preferably sufficient to prevent evaporation of volatile materials present.

The sulfonated asphalt product from the neutralization step is then treated for the removal of the solvent therefrom. In accordance with the present invention, such separation is performed by forming a moving film of the sulfonated asphalt on a heated surface under conditions adapted to simultaneously evaporate the solvent. More particularly, the separation of the solvent is performed by passing the same through an agitated or wiped-film evaporator. Removing solvent in this manner is substantially superior to conventional drum drying, since this procedure removes about 99.7% of the solvent, as compared with conventional drum drying, which removes about 75% of the solvent. As a result, solvent recovery is improved and subsequent drying of the sulfonated asphalt is less hazardous, more efficient and essentially free of pollutant production.

The separated sulfonated asphalt is in the form of an aqueous slurry at this point. Water is preferably removed in suitable drum-drying apparatus utilizing steam stripping. Sulfonated asphalt product and condensed water are withdrawn from the drum-drying system. However, the drum-drying system also produces a vapor phase containing small amounts of particulate sulfonated asphalt product. In accordance with the present invention, rather than directly venting this vapor phase to the atmosphere, the particulate sulfonated asphalt product is separated from the vapor phase as in a cyclone separator system, the separated particulate sulfonated asphalt is added to the sulfonated asphalt product from drying system and the remaining vapor phase is vented to the atmosphere.

Due to the nature of the solvent utilized and the temperatures utilized in the sulfonation and neutralization steps, vapor phases containing substantial amounts of solvent are produced in the sulfonation and neutralization steps. In accordance with the present invention, this solvent is recovered in an efficient recovery system, preferably, including, passage of the vapor phases from the sulfonation and neutralization steps to an appropriate knock-out drum for the removal of liquid and/or solid materials from the vapor, thereafter treating the resultant vapor to remove residual sulfonating agent, neutralizing agent and/or water by scrubbing with neutralizing agent solution, scrubbing with sulfuric acid or filtering, as by passing the same through a mist eliminator. Scrubbing with sulfuric acid can be carried out, for example, by utilizing a 95% sulfuric acid solution and has the added advantage of producing a saleable sulfuric acid solution. Passage of the vapor through a mist eliminator has the advantage of being significantly more efficient than scrubbing techniques. The utilization of a mist eliminator will also permit the utilization of less expensive piping and equipment downstream, to the extent that reduced amounts of sulfur trioxide are present in the vapor. Ultimately, recovered solvent and make-up solvent will be stored in an appropriate storage vessel which is also adapted to remove residual water from recovered solvent. Obviously, a vapor phase containing significant amounts of solvent would be present in the storage vessel. This vapor phase may be conveniently treated to remove residual water therefrom, as by passing the same through an appropriate knock-out drum. Vapor from the knock-out drum can be combined with vapors treated in the scrubbing or mist elimination steps. The storage vessel, as well as the previously mentioned knock-out drums, are at least intervally vented. Solvent recovered in the wiped film evaporator can be fed to an appropriate separating tank, which is appropriately vented at least intervally or, to the extent necessary, first cooling to separate a vapor phase from a liquid phase, passing condensed liquid to the previously mentioned tank and thence to the storage vessel and combining uncondensed vapor with the vapor from the storage vessel and from the scrubbers and/or mist eliminator. In accordance with the present invention, vapors from the solvent recovery means (wiped film evaporator) and the scrubbers and/or mist eliminator, as well as vent gases from the vented separation and storage vessels, are then treated to further purify the solvent, as by the removal of residual water therefrom. This is accomplished, in accordance with the present invention, by passing these vapors in indirect heat exchange with a refrigerant carried in a closed cycle compression-expansion system. Condensed liquid, primarily solvent but containing residual amounts of water, can be appropriately passed to a separator for separating the residual water therefrom. Purified solvent can then be passed to the solvent storage unit and uncondensed vapors recycled to indirect heat exchange with the refrigerant. This purification system will also produce a vapor phase containing from about 2% to 3% of solvent, in accordance with the present invention. In order to utilize this stream efficiently, this vapor is utilized as a fuel, as in a boiler system for generating in-plant steam or other in-plant fuel uses.

The operation and advantages of the present invention is further clarified and explained in the following description when read in conjunction with the drawings.

In accordance with FIG. 1, an asphalt feed is introduced to the system through line 10. As previously indicated, the asphalt material is preferably one having a softening point between about 315° F. and 350° F. Accordingly, the asphalt supply is maintained in a storage vessel 12 heated by hot oil circulated through line 14. The hot oil is preferably a crude oil heated to a temperature of about 475° F. Alternatively, where lower softening point asphalt, having a softening point between about 160° F. and 190° F. is utilized, the asphalt is fed through line 16 to storage vessel 18, which is heated by steam passing through line 20. In this case the steam has a temperature of about 300° F. The asphalt from storage vessel 12 or 18 is passed through lines 22 or 24, respectively, at a controlled rate. The solvent from the hereinafter mentioned storage vessel, preferably hexane, is introduced through line 26 at a controlled rate. The rate of flow of asphalt and solvent is also controlled at an appropriate predetermined ratio. The mixture of asphalt and solvent is passed through line 28. In order to produce a substantially uniform dispersion of the asphalt in the solvent, the mixture is preferably passed through an appropriate delumping or homogenizing means such as a colloid mill 30. The dispersion of asphalt and solvent is then fed to appropriately stirred and cooled sulfonation reactor 32. Sulfonating agent, preferably liquid sulfur trioxide, is introduced to the system through line 34 to an appropriate storage vessel 36. Sulfonating agent from storage vessel 36 is passed through line 38 at a controlled flow rate to sulfonation reactor 32. Where the rate of flow of sulfonating agent is controlled by passing the same through a speed controlled metering pump 40, vapors from sulfonating agent storage tank 36 will generally contain small amounts of sulfur trioxide which must be removed before venting such vapors to the atmosphere. Accordingly, such vapors are passed through line 42 to scrubber 44 where water supplied through line 46 is utilized to scrub out residual sulfur trioxide. The resultant sulfuric acid is discharged through line 48 to an appropriate storage vessel 50. As desired, a portion of the sulfuric acid may be recycled through line 52. Alternatively, the vapors from storage unit 36 may be passed through line 54 to a mist eliminator 56. Mist eliminators are well known to those skilled in the art and include fiber bed filters for the collection of liquid droplets, fogs and mists. Such filters are described in Kirk-Othmer, Vol. 1, 3rd Ed. at pages 694–696. A preferred mist eliminator is a Brinks-type unit, as illustrated in FIG. 17 of the reference. Separated sulfuric acid or sulfur trioxide from mist eliminator 56 can be passed to storage vessel 50 through line 58.

Separated liquid and/or solid unreacted materials and off spec sulfonated asphalt can be recycled to sulfonation reactor 32 through line 60. Sulfonic acid products are discharged from sulfonation reactor 32, as by means of a ram valve located at the bottom of the reactor and thence through line 62. Since there is a tendency to produce lumps of product in a sulfonation reaction, the effluent through line 62 is preferably passed through an appropriate delumper, such as a Franklin Miller pipe line delumper or equivalent. After an appropriate period of reaction within sulfonation reactor 32, for example about 30 minutes, the effluent reactor is automatically dumped by timed operation of an appropriate dump-type motor valve. Vapors produced in sulfonation reactor 32 and containing significant amounts of solvent are discharged through line 66 to the sulfonate recovery system hereinafter described with reference to FIG. 2.

Caustic is introduced to the system through line 68 to an appropriate storage vessel 70. From storage vessel 70, caustic is supplied through line 72 at a predetermined rate of flow to neutralization unit 74. The rate of flow of caustic is controlled by means of a speed controlled metering pump 76. The control of the rate of flow of caustic is, of course, coordinated with the rate of flow of asphalt, solvent and sulfonating agent. Caustic concentration within neutralizer 74 may be adjusted if necessary by the introduction of water through line 78. Neutralized product is discharged from neutralizer 74, as through an appropriate ram valve at the bottom of the neutralizer, following a predetermined period of reaction within neutralizer 74. Neutralized product is discharged through line 82 by means of an appropriate time-controlled, dump-type motor valve. The periodic dumping of neutralized product is also coordinated with the periodic dumping of sulfonic acid product and the flow rates of asphalt, solvent, sulfonating agent and neutralizing agent by means of a master time control or computer, which are, of course, well known to those skilled in the art. Vapors produced in neutralizer 74, and containing significant amounts of solvent, are discharged through line 84 to the solvent recovery system described with reference to FIG. 2.

Neutralized product from line 82 is fed to evaporator 86 for the removal of solvent. Evaporator 86 is an agitated or wiped film evaporator which operates by forming a film of the sulfonated asphalt or non-vaporizable material on the inner surface of an indirectly heated cylinder. A set of blades is rotated within the cylinder to maintain either a fixed, close clearance from the wall or actually ride on the film of liquid and/or solids and help carry the liquid as a film around and along the length of the heating surface. Such evaporators are well known to those skilled in the art and are generally described in Kirk-Othmer, Vol. 9, 3rd ed., at page 481. The specific evaporator utilized in accordance with the present invention is a vertical unit equipped with a condenser at the bottom of the unit. Sulfonated asphalt product is withdrawn through line 88 at the bottom of the wiped film heated section and a water-cooled condenser 90 at the bottom of the unit collects and recovers the solvent. Condensed solvent is discharged from the bottom of the condenser through line 92 whereas non-condensed solvent is discharged through line 94. Solvent discharged through lines 92 and 94, respectively, are passed to the solvent recovery system described with reference to FIG. 2 of the drawings.

Separated, sulfonated asphalt product passing through line 88 is fed to a vacuum-type double drum dryer 96. Such dryers are well known to those skilled in the art. Generally, metal drums heated, internally by steam through line 97, revolve slowly in contact with the slurry or solution to be dried. The dried product is removed from the drums by means of appropriate doctor knives. Dried sulfonated asphalt is discharged from the dryer through line 98 and the water removed in the dryer is discharged through line 100. A vapor phase produced in dryer 96 is discharged through line 102. This vapor usually contains small amounts of fine particle size sulfonated asphalt and is generally vented to the atmosphere. However, such venting creates pollution problems and, therefore, in accordance with another aspect of the present invention, the vapor passing through line 102 is passed to an appropriate gas-solids separating means, such as one or more cyclone separators 104. Separated particle-form sulfonated asphalt is passed through line 106 and added to the sulfonated asphalt product of line 98. Vapors from cyclone separator 104 are discharged to the atmosphere through line 106.

Figure 2:
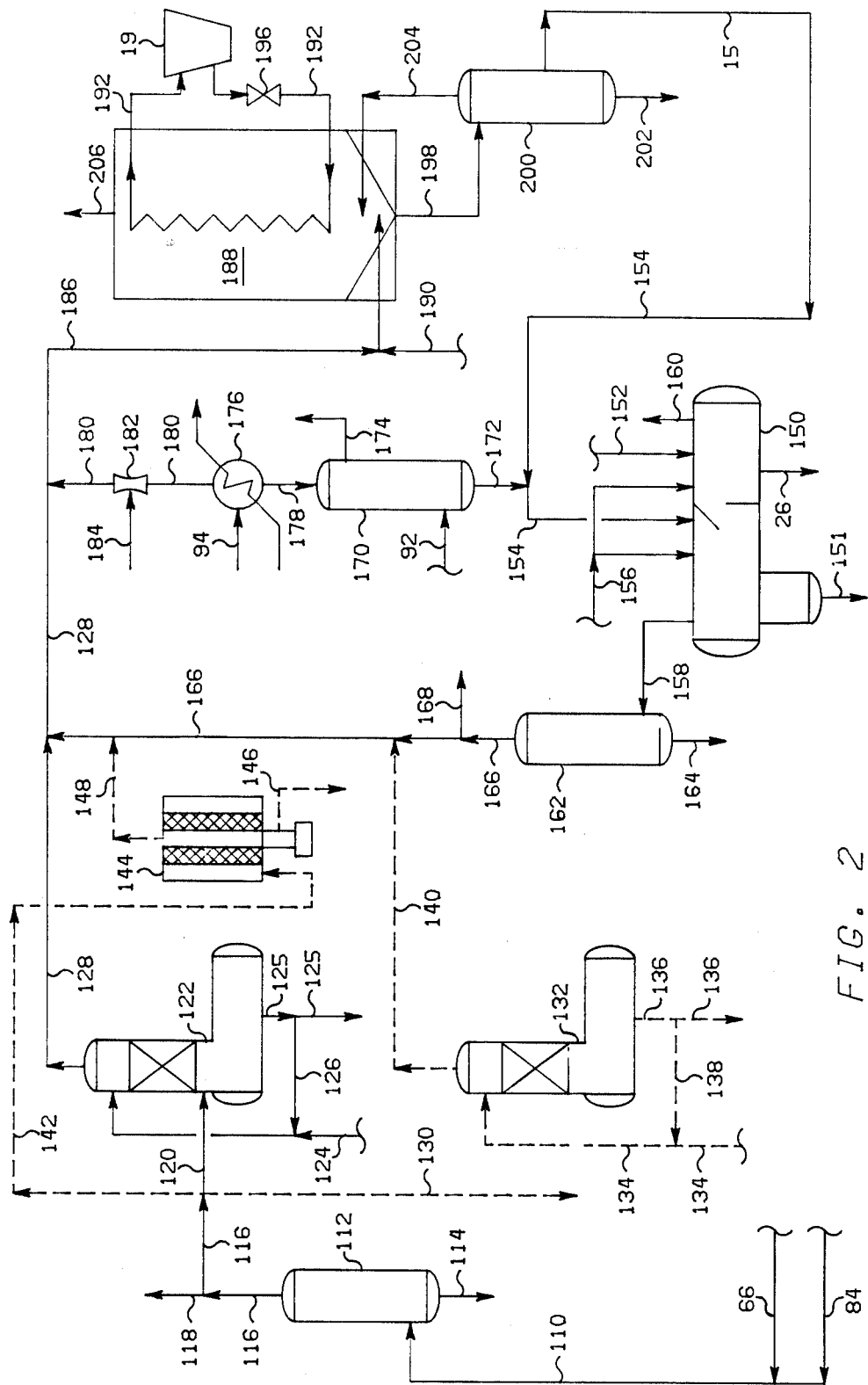
FIG. 2 schematically illustrates the preferred system for the recovery of solvent during the conduct of the process of FIG. 1.

The solid recovery system illustrated in FIG. 2 has numerous advantages, including, the recovery of maximum amounts of solvent, safety and the handling of flammable solvents, prevention of air pollution by vapors containing small amounts of solvent and complete utilization of normally unrecoverable solvent.

In accordance with FIG. 2, the vapors from sulfonation reactor 32 and neutralizer 74, which are discharged through lines 66 and 84, respectively, are combined and passed through line 110. The combined vapor streams in line 110 are fed to knock-out drum 112, removes liquid and/or solid materials from the vapor stream, including unreacted reactants and partially or fully reacted product, usually as a sludge. The sludge, thus separated in knock-out drum 112, is discharged through line 114 to an off specification tank (not shown) and is ultimately returned to the sulfonization reactor 32 through line 60 (FIG. 1). Clarified vapors are discharged through line 116 and are thereafter treated in one of several alternate fashions to additionally purify the same by the removal of unreacted reactants. At least intervally, knock-out drum 112 may be vented through line 118.

In one form of purifying the vapor stream passing through line 116, a stream is fed through line 120 to caustic scrubber 122. In caustic scrubber 122 the vapor is scrubbed by passing the same countercurrently to caustic introduced through line 124. Spent caustic is discharged through line 125, as spent caustic, or at least a portion thereof may be recycled through line 126. The purified vapor from caustic scrubber 122 is discharged through line 128. Alternatively, the vapors passing through line 116 can be passed through line 130 to sulfuric acid scrubber 132. In scrubber 132 the vapor passes countercurrently to sulfuric acid, usually 95% sulfuric acid solution, introduced through line 134. Since the unscrubbed vapors generally contain significant amounts of sulfur trioxide, this technique has the advantage that a saleable sulfuric acid solution is produced. This product is discharged through line 136 to a suitable storage area. At least a part of the discharged sulfuric acid may be recycled through line 138. Scrubbed vapors are discharged from scrubber 132 through line 140. Yet another alternative for purifying solvent vapors passing through line 116 is to pass the same through line 142 to a suitable mist eliminator 144. Such mist eliminators are known to those skilled in the art, as previously pointed out. This alternative has the further advantage that significantly larger amounts of the solvent contaminants are removed. The removed materials are discharged through line 146 to the off specification tank and, as previously pointed out, are fed back to the sulfonation reactor 32. Purified solvent is discharged from mist eliminator 144 through line 148. Solvent for use in the process of the present invention is stored in storage vessel 150 which also serves for the removal fo residual amounts of water, as hereinafter pointed out, which water is discharged through line 151. Make-up solvent is introduced to storage vessel 150 through line 152.

Solvent for use of the process is discharged from storage vessel 150 through line 26 which then is admixed with asphalt, as shown in FIG. 1. Recovered solvent is also introduced to storage tank 150 through line 154. In order to aid the removal of residual amounts of water from either make-up solvent or recovered solvent, fuel gas, hereinafter referred to, may be utilized by introduction through line 156. Vapors from storage vessel 150 are discharged through line 158. At least intervally, storage vessel 150 may be vented through line 160. The vapors from storage vessel 150 passing through line 158 are fed to knock-out drum 162 which removes residual liquid therefrom. The liquid is discharged through line 164 to the off specification storage tank and eventually back to sulfonation reactor 32 of FIG. 1. Vapors from knock-out drum 162 are discharged through line 166. At least intervally the knock-out drum may also be vented through line 168. Solvent recovered by wiped film evaporator 86 of FIG. 1 and passing through line 92 is fed to a lower level of collection tank 170 and thence as recovered solvent through line 172 and line 154 to storage vessel 150. Level tank 170 may also be, at least intervally, vented through line 174. Uncondensed solvent passing through line 94, from wiped film evaporator 86 of FIG. 1, is passed in indirect heat exchange with cooling water in condensor 176. Condensed solvent passes through line 178 to level tank 170 and ultimately to storage tank 150. Vapors are withdrawn from condensor 176 through line 180. This is accomplished by operating an eductor 182 by means of the hereinafter mentioned fuel gas introduced, through line 184. Solvent vapors passing through lines 128, 140 or 148 line 166 and line 180 are all combined in line 186. This vapor still contains residual amounts of water and, therefore, is fed to refrigeration unit 188 for further clarification. A significant feature of the present invention is that all of the vapors which are normally vented to the atmosphere and contain significant amounts of solvent, particularly all of the vapors vented from the solvent recovery system of FIG. 2, are collected and also introduced to refrigeration unit 180 through line 190. This, of course, improves solvent recovery, reduces hazards near the vents and obviously reduces pollution of the air. In refrigeration unit 188, the vapor is passed in indirect heat exchange with a suitable refrigerant passing through a closed cycle refrigerant system 192, including compressors as represented by 194 and expansion means as represented by expansion valve 196. Obviously, closed cycle refrigeration system is greatly simplified in the drawing. In any event, refrigeration unit 188 condenses substantially all of the solvent and discharges the same through line 198. From line 198 the condensed solvent is introduced to an appropriate separator 200. In separator 200 residual water or other phase-separable material is discharged to a waste water facility through line 202 and the recovered solvent is discharged from separator 200 through line 154 to solvent storage vessel 150. Any vapor state materials from separator 200 are recycled to refrigeration unit 188 through line 204. A noncondensed gas phase comprising primarily air, but containing about 2 to 3 percent of solvent is discharged from refrigeration unit 188 through line 206. Accordingly, to the extent that the solvent is a flammable material, such as hexane, this gas phase can be utilized as a supplemental fuel to an in-plant boiler, which in turn is utilized to produce steam. It can of course be utilized in conjunction with other fuels, thus supplying air for combustion along with combustible solvent. Other fuel requirements of the plant may also be served in a like manner. The fuel gas, as previously indicated, can also be utilized by passing the same through line 156 to storage unit 150 and to operate eductor 182.

While the present invention has been described with reference to specific reactants, operating conditions, modes of operation and equipment, it is to be understood that these specific recitals are by way of illustration and to set forth the best mode in accordance with the present invention and are not to be considered limiting. Accordingly, the invention is to be limited only in accordance with the appended claims.

That which is claimed:

1. A process for producing sulfonated asphalt comprising:
   (a) adding a normally liquid, inert, low boiling solvent to an asphaltic material;
   (b) contacting the thus formed mixture of asphaltic material and solvent with a liquid sulfonating agent under sulfonation conditions;
   (c) neutralizing the thus produced sulfonic acids with a basic neutralizing agent under neutralizing conditions;
   (d) separating said solvent from the thus produced sulfonated asphalt by forming a moving film of said sulfonated asphalt on a heated surface under conditions adapted to simultaneously evaporate said solvent;
   (e) recovering the thus evaporated solvent; and
   (f) drying the thus separated sulfonated asphalt as a product of the process, wherein vapor phases containing significant amounts of solvent are withdrawn from at least one of the sulfonation step and the neutralization step and solvent is recovered therefrom by one of (1) countercurrently scrubbing said vapor phase with a portion of the neutralizing agent, (2) countercurrently scrubbing said vapor phase with an aqueous solution of sulfuric acid and (3) passing said vapor phase through a fiber-type filter means to purify the same.

2. A process in accordance with claim 1 wherein the thus purified solvent is in a vapor phase, a refrigerant is subjected to alternate compression and expansion in a closed cycle refrigeration system and essentially all of said purified solvent is further purified and condensed for reuse by passing the same in indirect heat exchange with said refrigerant.

3. A process in accordance with claim 2 wherein a portion of the solvent is separated from the sulfonated asphalt in the separation step in a liquid phase and the remainder is separated in a vapor phase, said liquid phase portion of said solvent is withdrawn for reuse in the process and at least part of said vapor phase portion of said solvent is combined with the purified solvent and further purified and condensed in the refrigeration step.

4. A process in accordance with claim 3 wherein solvent for use and reuse in the process is stored in at least one storage step, a vapor phase containing significant amounts of solvent is withdrawn from at least one of said storage steps and liquid and/or solid phases are separated from at least one of the vapor phase thus withdrawn from said storage step, the vapor phase withdrawn from the sulfonation step and the vapor phase withdrawn from the neutralization step in at least one clarification step.

5. A process in accordance with claim 4 wherein vapor phases containing significant amounts of solvent are at least intervally vented from at least one of the storage steps and the clarification steps and at least one of the thus vented vapor phases is further purified and condensed in the refrigeration step.

6. A process in accordance with claim 5 wherein a vapor phase containing noncondensed solvent is withdrawn from the refrigeration step for use as a fuel.

7. A process for producing sulfonated asphalt, comprising:
 (a) adding a normally liquid, inert, low boiling solvent to an asphaltic material;
 (b) contacting the thus formed mixture of asphaltic material and solvent with a liquid sulfonating agent under sulfonation conditions;
 (c) neutralizing the thus produced sulfonic acids with a basic neutralizing agent under neutralizing conditions;
 (d) separating at least part of said solvent, in a vapor phase, from the thus produced sulfonated asphalt;
 (e) subjecting a refrigerant to alternate compression and expansion in a closed cycle refrigeration system;
 (f) passing the thus separated solvent in indirect heat exchange with the refrigerant at a temperature sufficient to purify, condense and recover essentially all of said solvent for reuse; and
 (g) drying the thus separated sulfonated asphalt as a product of the process.

8. A process in accordance with claim 7 wherein vapor phases containing significant amounts of solvent are withdrawn from at least one of the sulfonation step and the neutralization step, the thus withdrawn solvent is preliminarily purified by one of (1) countercurrently scrubbing said vapor phase with a portion of the neutralizing agent, (2) countercurrently scrubbing said vapor phase with an aqueous solution of sulfuric acid and (3) passing said vapors through a fiber-type filter means and the thus purified solvent is thereafter further purified in the refrigeration step.

9. A process in accordance with claim 8 wherein a portion of the solvent is separated from the sulfonated asphalt in the separation step in a liquid phase and the remainder is separated in a vapor phase, said liquid phase portion of said solvent is withdrawn for reuse in the process and at least part of said vapor phase portion of said solvent is combined with the preliminarily purified solvent and further purified in the refrigeration step.

10. A process in accordance with claim 9 wherein solvent for use and reuse in the process is stored in at least one storage step, a vapor phase containing significant amounts of solvent is withdrawn from at least one of said storage steps and liquid and/or solid phases are separated from at least one of the vapor phase thus withdrawn from said storage step, the vapor phase withdrawn from the sulfonation step and the vapor phase withdrawn from the neutralization step in at least one clarification step.

11. A process in accordance with claim 10 wherein vapor phases containing significant amounts of solvent are at least intervally vented from at least one of the storage steps and the clarification steps and at least one of the thus vented vapor phases is further purified, condensed and recovered for reuse in the refrigeration step.

12. A process in accordance with claim 11 wherein a vapor phase containing noncondensed solvent is withdrawn from the refrigeration step for use as a fuel.

13. A process for producing sulfonated asphalt comprising:
 (a) adding a normal liquid, inert, low boiling solvent to an asphaltic material;
 (b) reducing the size of larger particles of said asphaltic material to produce an essentially uniform dispersion of said asphaltic material in said solvent;
 (c) contacting the thus formed dispersion of asphaltic material in solvent with a liquid sulfonating agent under sulfonation conditions;
 (d) neutralizing the thus produced sulfonic acids with a basic neutralizing agent under neutralizing conditions;
 (e) separating the said solvent from the thus produced sulfonated asphalt;
 (f) recovering the thus evaporated solvent; and
 (g) drying the thus separated sulfonated asphalt as a product of the process.

14. A process in accordance with claim 13 wherein the size of large particles of the asphaltic material is reduced by passing the same through a colloid mill.

15. A batch-type process for producing sulfonated asphalt comprising:
 (a) adding a normally liquid, inert, low boiling solvent, at a predetermined flow rate, to a stream of asphaltic material, flowing at a predetermined flow rate;
 (b) adding a liquid sulfonating agent at a predetermined flow rate to the thus formed mixture of asphaltic material and solvent and contacting the same under sulfonation conditions in a sulfonation zone;
 (c) withdrawing the thus produced sulfonic acids from said sulfonation zone at the end of a predetermined period of time;
 (d) adding a basic neutralizing agent at a predetermined flow rate to the thus produced sulfonic acid and contacting the same under neutralizing conditions in a neutralization zone;
 (e) withdrawing the thus produced sulfonated asphalt from said neutralization zone at the end of a predetermined period of time;
 (f) separating said solvent from said sulfonated asphalt; and
 (g) drying the thus separated sulfonated asphalt as a product of the process;
 (h) said rates of flow of said solvent, said asphaltic material, said sulfonating agent and said neutralizing agent and said periods of time prior to said withdrawal of said sulfonic acids and said said sulfonated asphalt being selected to maintain essentially continuous flow of said solvent, said asphaltic material, said sulfonating agent and said neutralizing agent.

16. A process in accordance with claim 15 wherein the sulfonating agent and the neutralizing agent are added at predetermined flow rates by passing the same through metering pumps.

17. A process in accordance with claim 16 wherein the rates of flow of the solvent and the asphaltic material, the rates of speed of the metering pumps adding the sulfonating agent and the neutralizing agent and the periods of time prior to the withdrawal of the sulfonic acids and the sulfonated asphalt are coordinated in accordance with a predetermined time cycle.

18. A process in accordance with claim 15 wherein flow rates of the solvent, the asphaltic material, the sulfonating agent, and the neutralizing agent and the periods of time prior to the withdrawal of the sulfonic acids and the sulfonated asphalt are coordinated in accordance with a predetermined time cycle.

19. A process for producing sulfonated asphalt comprising:
   (a) adding a normally liquid, inert, low boiling solvent to an asphaltic material;
   (b) contacting the thus formed mixture of asphaltic material and solvent with a liquid sulfonating agent under sulfonation conditions;
   (c) neutralizing the thus produced sulfonic acids with a basic neutralizing agent under neutralizing conditions;
   (d) separating said solvent from the thus produced sulfonated asphalt by evaporating said solvent therefrom;
   (e) recovering the thus separated solvent for reuse;
   (f) drying the thus separated asphalt to produce a dry sulfonated asphalt as a product of the process under conditions which also produce a vapor phase containing sulfonated asphalt particles;
   (g) separating said sulfonated asphalt particles, as an additional product of the process, from said vapor phase containing said sulfonated asphalt particles; and
   (h) venting the thus separated vapor phase to the atmosphere.

20. A process in accordance with claim 19 wherein the sulfonated asphalt particles are separated from the vapor phase containing said sulfonated asphalt particles by passing the same through at least one cyclone separator.

21. A process in accordance with claim 20 wherein the separated sulfonated asphalt is dried by passing the same through at least one drum dryer.

* * * * *